US005646031A

United States Patent [19]
DeYoung et al.

[11] Patent Number: 5,646,031
[45] Date of Patent: Jul. 8, 1997

[54] SARMV AND SCYMVI HAIRPIN RIBOZYMES

[75] Inventors: Mary Beth DeYoung, Elmhurst; Andrew M. Siwkowski, Sycamore; Arnold E. Hampel, DeKalb, all of Ill.

[73] Assignee: Northern Illinois University, DeKalb, Ill.

[21] Appl. No.: 442,513

[22] Filed: May 16, 1995

[51] Int. Cl.$^6$ .......... C07H 21/04; C12Q 1/68; A61K 48/00; C12N 15/85

[52] U.S. Cl. .......... 435/325; 435/6; 435/91.31; 435/172.1; 435/172.3; 435/252.3; 435/320.1; 536/23.1; 536/23.2; 536/24.5; 514/44

[58] Field of Search .......... 435/6, 91.31, 172.1, 435/172.3, 320.1, 240.1, 240.2, 252.3; 536/23.1, 23.2, 24.5; 514/44

[56] References Cited

U.S. PATENT DOCUMENTS

| | | | |
|---|---|---|---|
| 5,093,246 | 3/1992 | Cech et al. | 435/91.31 |
| 5,144,019 | 9/1992 | Rossi et al. | 536/23.2 |
| 5,225,337 | 7/1993 | Robertson et al. | 435/91.31 |
| 5,225,347 | 7/1993 | Goldberg et al. | 435/320.1 |
| 5,254,678 | 10/1993 | Haseloff et al. | 536/23.2 |

OTHER PUBLICATIONS

Altschuler et al., "Method for generating transcripts with defined 5' and 3' termini by autolytic processing" *Gene*, 122:85–90 (1992).

Anderson et al., "Mutagenesis of the hairpin ribozyme" *Nucleic Acids Res.*, 22: 1096–1100 (1994).

Berzal–Harranz et al., "Essential nucleotide sequences and secondary structure elements of the hairpin ribozyme" *EMBO J.*, 12:2567–2573 (1993).

Buzayan et al., "Nucleotide sequence of satellite tobacco ringspot virus RNA and its relationship to multimeric forms" *Virology*, 151:186–199 (1986).

Cech, "RNA as an enzyme" *Scientific American*, 255:64–75 (1986).

Cech, "Self–splicing of Group I introns" *Annu. Rev. Biochem.*, 59:543–568 (1990).

Fritsch et al., "Properties of satellite RNA of nepoviruses" *Biochemie*, 75:561–567 (1993).

Gilboa et al., "Transfer and expression of clones genes using retroviral vectors" *BioTechniques*, 4(6):504–512 (1986).

Hampel and Tritz, "RNA catalytic properties of the minimum (–)sTRSV sequence" *Biochemistry*, 28:4929–4933 (1989).

Hampel et al., "Hairpin catalytic RNA model: evidence for helices and sequence requirement for substrate RNA" *Nucleic Acids Research*, 18:299–304 (1990).

Hampel et al., "The hairpin ribozyme" *Methods: A Comparison to Methods in Enzymology*, 5:37–42 (1993).

Haseloff and Gerlach, "Simple RNA enzymes with new and highly specific endoribonuclease activities" *Nature*, 334:585–591 (1988).

Haseloff and Gerlach, "Sequences required for self–catalyzed cleavage of the satellite RNA of tobacco ringspot virus" *Gene*, 82:43–52 (1989).

Kaper et al., "Nucleotide sequence predicts circularity and self–cleavage of 300–ribonucleotide satellite of arabis . . . " *Biochem. Biophys. Res. Com.*, 154:318–325 (1988).

Milligan et al., "Oligoribonucleotide synthesis using T7 RNA polymerase and synthetic DNA templates" *Nucleic Acids Res.*, 15:8783–8798 (1987).

Ojwang et al., "Inhibition of human immunodeficiency virus type–I (HIV–1) expression by a hairpin ribozyme" *Proc. Nat. Acad. Sci. USA*, 89:10802–10806 (1992).

Perriman et al., "Extended target–site specificity for a hammerhead ribozyme" *Gene*, 113:157–163 (1992).

Rubino et al., "Nucleotide sequence and structural analysis of two satellite RNAs associated with chicory yellow mottle virus" *J. General Virology*, 7:1897–1903 (1990).

Santa Lucia et al., "Effects of GA mismatches on the structure and thermodynamics of RNA internal loops" *Biochemistry*, 29:8813–8819 (1990).

Siwkowski et al., "Catalytic properties of hairpin–like ribozymes derived from CYMV . . . " Presented at *RNA Processing Meeting: Cold Spring Harbor*, Cold Spring Harbor, NY, (Poster)(May, 1995).

Sullivan, "Development of ribozymes for gene therapy" *J. Investigative Dermatology (Suppl)*, 103:95s (1994).

Symons, "Self–cleavage of RNA in the replication of small pathogens of plants and animals" *TIBS*, 14:445–450 (1989).

Symons, "Small catalytic RNAs" *Annu. Rev. Biochem.*, 61:641–671 (1992).

Uhlenbeck, "Small catalytic oligoribonucleotide" *Nature*, 328:596–600 (1987).

Yamada et al., "Intracellular immunization of human T cells with hairpin ribozyme against human immunodeficiency virus type 1" *Gene Therapy*, 1:38–45 (1994).

Yu et al., "A hairpin ribozyme inhibits expression of diverse strains of human immunodeficiency virus type 1" *Proc. Nat. Acad. Sci. USA*, 90:6340–6344 (1993).

Wong–Staal and Nabel, "Is HIV's achilles heel hidden in its genes" *HIV Advances in Res. and Therapy*, 4:3–8 (1994).

*Primary Examiner*—John L. LeGuyader
*Attorney, Agent, or Firm*—Kohn & Associates

[57] ABSTRACT

A method for the identification by modeling of synthetic catalytic RNAs and ribozymes thereof are disclosed including a hairpin portion and binding sites for cleaving an RNA substrate at a site which has a GUA sequence following the site of cleavage. Synthetic catalytic RNA has been modeled from negative strands of satellite RNA from the group consisting of chicory yellow mottle virus (sCYMVI) and arabis mosaic virus (sArMV).

6 Claims, 4 Drawing Sheets

SARMV AND SCYMVI HAIRPIN RIBOZYMES

GRANT SUPPORT

Research in this application was supported in part by a grant from the National Institutes of Health to AEH (AI29870). The Government has certain rights in the invention.

TECHNICAL FIELD

The present invention is in the general area of a RNA catalyst, i.e., ribozyme, and methods of modeling new hairpin ribozymes as well as two new hairpin ribozymes.

BACKGROUND OF THE INVENTION

Ribozymes are RNA molecules that possess RNA catalytic ability (see Cech, 1986, 1990, for review) that cleave a specific site in a target RNA substrate in a trans reaction. The catalytic ability is shown in that the number of RNA molecules that are cleaved by a ribozyme is greater than the number predicted by stochiochemistry (Hampel and Tritz, 1989; Uhlenbeck, 1987).

Ribozymes catalyze the phosphodiester bond cleavage of RNA and are emerging as a new tool for controlling the cellular RNA levels of specific genes. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs or viral RNA genomes for gene therapy (Sullivan, 1994).

U.S. Pat. No. 5,093,246 issued to Cech et al. discloses an endoribonuclease that has an eight base pair active site which hybridizes to a target RNA sequence whereafter cleavage of the target RNA takes place, with a requirement for free guanosine or guanosine derivatives. The limited number of nucleotides available for hybridization to an RNA substrate has been found to limit the efficiency of the Cech endoribonuclease. A number of nucleotides in the active site of the Cech endoribonuclease have been found to need to be conserved for efficient endoribonuclease activity. This restricts the number of permutations of active site sequences which can be engineered to effect hybridization to target sequences, thereby restricting the range of RNA target sequences cleavable by the Cech endoribonuclease. The Cech endoribonuclease also modifies the RNA substrate by adding a free guanosine nucleotides to the 5' end of cleaved RNA.

U.S. Pat. No. 5,254,678 issued to Hasseloff et al. discloses a hammerhead ribozyme. The catalytic region in the hammerhead ribozyme is in reverse order to that of the hairpin ribozyme as described herein below. The hammerhead ribozyme is not as efficient in vivo as the hairpin ribozyme. The hammerhead ribozyme has not been approved for human clinical trials.

A hairpin ribozyme has been developed by the applicants which successfully cleaves HIV-1 genomic and mRNAs in vitro and in cells (Ojwang et al., 1992; Yu et al., 1993). This HIV-1 specific hairpin ribozyme is being prepared for clinical testing in human AIDS patients (Wong-Staal, 1994). Given the therapeutic potential of the hairpin ribozyme, as well as the general importance of a designed "molecular knife", it would be useful to have additional hairpin ribozymes.

However, currently such ribozymes are identified empirically. It would be useful to have a method whereby any nucleotide sequence can be screened to identify new sequences with catalytic activity. Further, hairpin ribozymes that are currently available cleave an RNA substrate within the catalytic region at a site which has a GUC sequence following the site of cleavage. It would be useful to have hairpin ribozymes which can cleave at additional sites.

SUMMARY OF THE INVENTION AND ADVANTAGES

According to the present invention, a synthetic catalytic RNA is disclosed including a hairpin portion and binding sites for cleaving an RNA substrate at a site which has a GUA sequence following the site of cleavage. The synthetic catalytic RNA is modeled from negative strands of satellite RNA from the group consisting of chicory yellow mottle virus (sCYMV1) and arabis mosaic virus (sArMV).

According to the present invention, a method of identification by modeling of a hairpin ribozyme whereby sequence and structural homologies are identified is disclosed. The method includes the steps of searching databases, such as GenBank, which contain genetic sequences for short nucleotide sequences homologous to the sTRSV hairpin ribozyme at conserved homologous regions from Loop 2 through Loop 4 of sTRSV. The sTRSV ribozyme sequence is then aligned with the identified sequence and structural analysis is undertaken whereby Helices 3 and 4 are identified followed by Loop 3. The next step is to determine the ribozyme strands of Helix 2, Helix 1 and Loop 1 and the substrate target region segments which will base pair with the ribozyme to form Helices 1 and 2, as well as Loop 5. This method allows the identification of new hairpin ribozymes and hairpin ribozymes that do not require the GUC sequence in the cleavage region as found in sTRSV.

Expanding the availability of hairpin ribozymes to cleave substrates which have a GUA or GUG sequence following the site of cleavage are useful in providing new reagents used for cleaving isolated RNA, as well as for antiviral therapeutics. For example, the cleavage reaction can be used in vitro to produce large quantities of specific RNA fragments. The ribozymes are also useful as diagnostics for the detection of viruses containing the cleavage site in biological samples.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The present invention provides a synthetic catalytic RNA, i.e. ribozyme, including a hairpin portion and binding sites for cleaving an RNA substrate in a trans position at a site which has a GUA sequence following the site of cleavage. Further, the present invention provides a ribozyme, including a hairpin portion and binding sites for cleaving an RNA substrate in a trans position at a site which has a GUG sequence following the site of cleavage.

"Synthetic RNA catalyst", or ribozyme, as used herein, means a catalyst which is not a naturally-occurring RNA catalyst, although "synthetic catalysts" may be truncated or altered versions of naturally-occurring catalysts. The ribozyme cleaves the substrate in a trans position at a specific site to produce a fragment having an OH at the 5' end and a fragment having a 2',3' cyclic phosphate at the 3' end. "Synthetic catalyst" include catalysts synthesized in vitro and catalysts synthesized in vivo. In particular, "synthetic catalysts" can include catalysts produced by hosts transformed by a vector comprising a sequence coding for the catalyst.

SUBSTRATE

RNA of any length and type may be used as the substrate as long as it contains the target sequence represented by the formula 5'-$F_1$-CS-$F_2$-3'. In this formula, CS is the cleavage sequence, i.e., a sequence of bases containing the site at which the catalyst cleaves the substrate. CS is a short sequence of bases which does not base pair with the ribozyme and can also be referred to as Loop 5 ($L_5$). In a preferred embodiment of the present invention, CS preferably has the sequence 5'-NGUA-3', wherein N is any base, and the substrate is cleaved by the ribozyme between N and G to produce a fragment having an OH at the 5' end and a fragment having a 2,'3' cyclic phosphate at the 3' end. In a second embodiment of the present invention, CS preferably has the sequence 5'-NGUG-3', wherein N is any base, and the substrate is cleaved by the ribozyme between N and G to produce a fragment having an OH at the 5' end and a fragment having a 2,'3' cyclic phosphate at the 3' end.

Loop 5 (CS) is flanked by two short base sequences $F_1$ and $F_2$ which do base pair with the RNA catalyst. $F_1$ is preferably at least three bases in length, most preferably four bases in length. $F_2$ is also preferably at least three bases in length, most preferably six to twelve bases in length.

RIBOZYMES

Figure 1A:
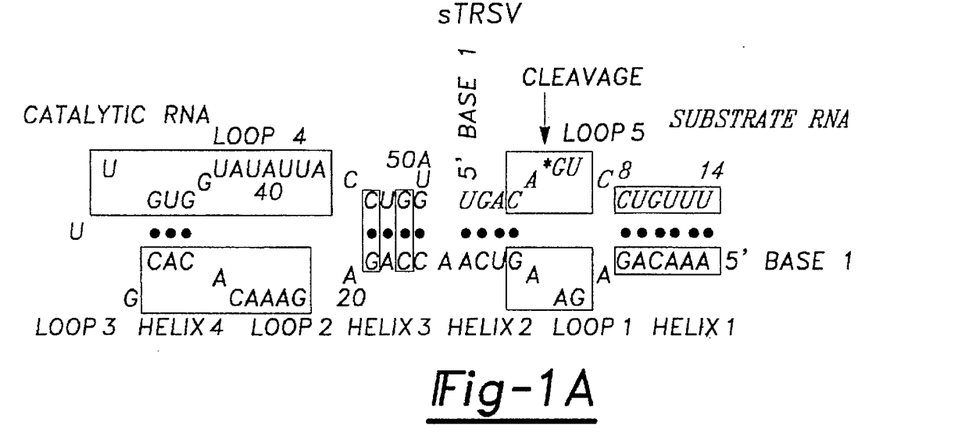
FIGS. 1A–C are schematic representations of the hairpin ribozyme/substrate complex, (A) sTRSV origin, (B) sCYMV1 origin, (C) sArMV origin, ribozyme and substrate RNAs are numbered sequentially from 5' to 3' and boxed regions are conserved in all three.
Figure 1B:
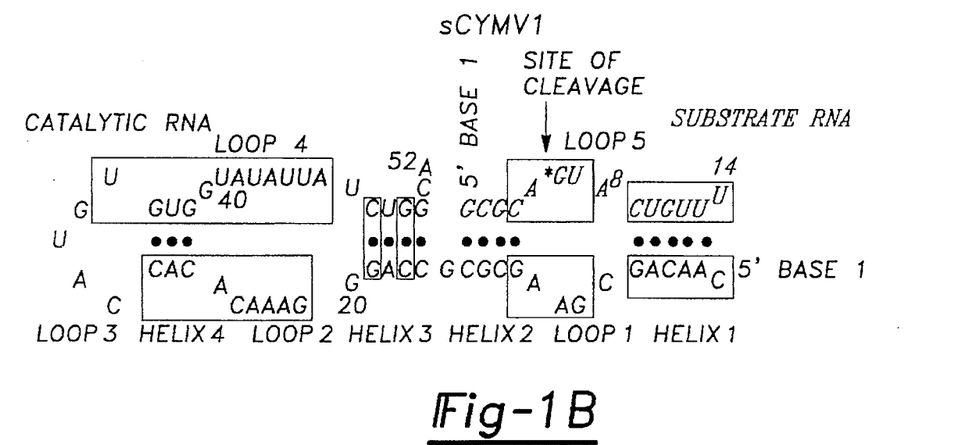
Figure 1C:
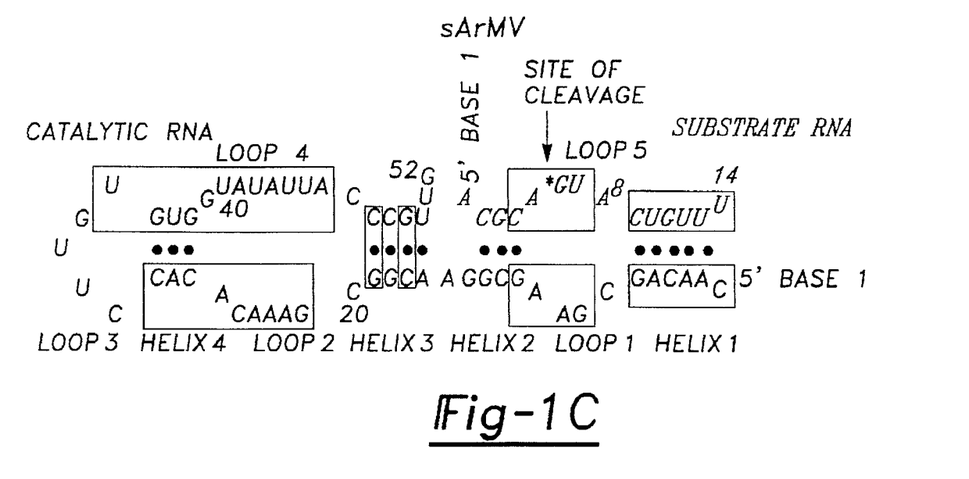

Ribozymes, according to the present invention, also include a substrate binding portion and a "hairpin" portion. The substrate binding portion of the catalyst is represented by the following formula:

In this formula the terms are defined as follows:

$F_3$ is a sequence of nucleotides (bases) selected so that when the catalyst is bound to the substrate, $F_3$ is substantially base paired with $F_2$ forming Helix 1 (FIGS. 1A–C).

$F_4$ is a sequence of nucleotides selected so that $F_4$ is substantially base paired with $F_1$ when the catalyst is bound to the substrate thereby forming Helix 2 (FIGS. 1A–C).

The sequences of $F_3$ and $F_4$ are selected so that each contains an adequate number of nucleotides to achieve sufficient binding of the RNA substrate to the RNA catalyst so that cleavage of the substrate can take place. $F_3$ is preferably at least three nucleotides in length, most preferably from six to twelve nucleotides in length. $F_4$ is preferably from three to five nucleotides in length, most preferably four nucleotides in length.

$L_1$ (Loop 1) is a sequence of nucleotides selected so that $L_1$ does not base pair with CS (Loop 5) when the catalyst is bound to the substrate and which may have the sequence 5'-CGAA-3' when CS has the sequence 5'-NGUA-3'.

As used herein, "substantially base paired" means that greater than 65% of the nucleotides of the two RNA sequences in questions are base paired, and preferably greater than 75% of the nucleotides are base paired. "Substantially unpaired" means that greater than 65% of the nucleotides of the two sequences in questions are not base paired, and preferably greater than 75% of the nucleotides are not paired.

The "hairpin" portion is a portion of the catalyst which folds into a hairpin-like configuration when the substrate-catalyst complex is modeled in two dimensions for minimum energy folding. This is shown in FIGS. 1A–C. The "hairpin" portion is not an absolute hairpin in the sense that not all nucleotides of the "hairpin" portion are base-paired. Indeed, it is necessary for the "hairpin" portion to have at least one substantially unpaired region so that the catalyst can assume a tertiary structure that allows for better, or optimal, catalytic activity.

The "hairpin" portion of the catalyst preferably has the formula:

```
    P₃—L₄—P₄-3'
   /
  L₃
   \
    P₂—L₂—P₁-5'
``` wherein, $P_1$ and $P_4$ are nucleotide sequences selected so that $P_1$ and $P_4$ are substantially base paired forming Helix 3 (FIGS. 1A–C) and are each preferably from three to six nucleotides in length;

$P_1$ is covalently attached to $F_4$;

$L_4$ (Loop 4) and $L_2$ (Loop 2) are sequences selected so that they are substantially unpaired and are each preferably from four to nine nucleotides in length;

$P_2$ and $P_3$ are nucleotide sequences selected so that $P_2$ and $P_3$ are substantially base paired forming Helix 4 (FIGS. 1A–C); and $L_3$ (Loop 3) is a sequence of unpaired nucleotides and forms the "bend" in the hairpin configuration.

"Substantially base paired" and "substantially unpaired" have the same meanings as discussed herein above.

In the prior art ribozyme, sTRSV, the preferred sequence for $P_2$ is 5'-CAC-3', for $P_3$ is 5'-GUG-3' and for $L_3$ is 5'-GUU-3' as shown in FIG. 1A (Anderson et al., 1994). The prior art ribozyme, sTRSV, has a sequence of In an embodiment of the ribozymes, Loop 3 is replaced with a tetraloop modification (Anderson et al., 1994).

The sTRSV hairpin ribozyme (FIG. 1A) has a well-defined hairpin-like secondary structure which applicants named the hairpin (Tritz and Hampel, 1989; Hampel et al., 1990; Hampel et al., 1993). Mutagenesis data have identified and confirmed the presence of four primary helices and five loops in the RNA structure (Hampel et al., 1990; Anderson et al., 1994; Berzal-Herranz et al., 1993). The ribozyme can be adapted to cleave non-native substrates by modifying the bases in Helices 1 and 2 to complement the mRNA of choice.

The sequences of the satellite RNAs of chicory yellow mottle virus (sCYMV1) and arabis mosaic virus (sArMV) are known. The sCYMV1 sequence is 457 nucleotides (nt) (Rubino et al., 1990) and 300 nt for sArMV (Kaper et al., 1988) compared to 359 nt for sTRSV (Buzayan et al., 1986; Fritsch et al., 1993).

Using the method of the present invention as described herein below, the sCYMV1 ribozyme (FIG. 1B) and sArMV ribozyme (FIG. 1C) were constructed.

The sequences used for sCYMV1 ribozyme differs from that of the sTRSV derived ribozyme by 4 nt in the substrate and 13 nt in the ribozyme for an overall base composition difference of 27%. The sArMV ribozyme sequence differs from sTRSV by 4 nt and 16 nt in substrate and ribozyme sequences, respectively, for an overall difference of 31%.

```
sTRSV ribozyme                                                    (SEQ ID No:1)

AAACAGAGAA  GUCAACCAGA  GAAACACACG  UUGUGGUAUA  UUACCUGGUA
    10          20          30          40          50
```

The present invention includes a synthetic catalytic RNA, ribozyme, wherein the synthetic catalytic RNA is modeled from the negative strand of satellite RNA from chicory yellow mottle virus (sCYMVI) including a hairpin portion and binding sites for cleaving an RNA substrate at a site which has a GUA sequence following the site of cleavage. The ribozyme is named based on the viral origin. This ribozyme has a two-dimensional configuration shown in FIG. 1B and has the following nucleotide sequence in a preferred embodiment.

The sCYMV1 and sArMV sequences differ from each other in only 1nt in the substrate and 11 nt in the ribozyme for an overall difference of 23%.

Both the sCYMV1 and sArMV ribozyme can be modeled in a hairpin-type motif analogous to the known four helical domains and known five-loop domains of the sTRSV hairpin ribozyme. Helix 2, however, for the native substrate sequence, is 3 bp in the sArMV sequence as compared to 4 bp for the sTRSV and sCYMV1 sequences.

Sequence and probable structural similarities of sCYMV1 and sArMV ribozymes with the sTRSV hairpin ribozyme

```
sCYMV1 ribozyme                                                   (SEQ ID No:2)

CAACAGCGAA  GCGCGCCAGG  GAAACACACC  AUGUGUGGUA  UAUUAUCUGG  CA
    10          20          30          40          50
```

The present invention further includes a synthetic catalytic RNA, ribozyme, wherein the synthetic catalytic RNA is modeled from the negative strand of satellite RNA from arabis mosaic virus (sArMV) including a hairpin portion and binding sites for cleaving an RNA substrate at a site selected from the group consisting of a GUA sequence following the site of cleavage and a GUG sequence following the site of cleavage. This ribozyme has a two dimensional configuration as shown in FIG. 1C and has the following nucleotide sequence in a preferred embodiment.

indicate that they are likely members of the hairpin ribozyme family. While the sequence homology is diverse, the structural similarities, following applicants' sTRSV hairpin ribozyme rules, within the proposed models are present. Major sequence differences are mostly in regions of non-required sequence for sTRSV hairpin ribozyme, with the most significant differences being in Loop 3 which is known not to have required nucleotides (Anderson et al., 1994).

The present invention provides for a compound comprising the sCYMV1 or sArMV ribozymes in combination with

```
sArMV ribozyme                                                    (SEQ ID No:3)

CAACAGCGAA  GCGGAACGGC  GAAACACACC  UUGUGUGGUA  UAUUACCCGU  UG
    10          20          30          40          50
``` pharmaceutically, veterinarially or agriculturally acceptable carriers. According to the present invention, however, any vehicle, diluent, or additive used would have to be compatible with the ribozyme and not reduce its biological activity.

The present invention also provides a vector comprising a DNA sequence encoding the sCYMV1 or sArMV ribozymes with the DNA being operatively liked to expression control sequences. The present invention further provides a host cell, either prokaryotic or eukaryotic, transformed with either vector wherein the host cell is capable of expressing the ribozyme.

Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses, such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Spring Harbor Laboratory Press, New York (1992); in Ausubel et al., *Current Protocols in Molecular Biology*, John Wiley and Sons, Baltimore, Md. (1989); Chang et al., *Somatic Gene Therapy*, CRC Press, Ann Arbor, Mich. (1995); Vega et al., *Gene Targeting*, CRC Press, Ann Arbor, Mich. (1995); and Gilboa et al. (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells for therapeutic utilization. Viral vectors can also be modified with specific receptors or ligands to alter target specificity through receptor mediated events.

The present invention also provides a method for identification by modeling of new hairpin ribozymes. A modeling protocol for ribozyme was proposed by Rubino et al (1990). However, this protocol utilized the entire sequence of sTRSV for screening and, therefore, is not as efficient in identification as the present method. The method of the present invention allows identification of new ribozymes with only short homologous sequences and expands the repertoire of clearable target sites within RNA sequences since it is not limited to a GUC sequence following the cleavage site in the substrate.

The method includes the steps of screening databases, such as GenBank, which contain nucleotide sequences to identify sequences homologous to a conserved sTRSV ribozyme sequences of Loop 2 and Loop 4 (Anderson et al, 1994), with an expect number of 999. The nucleotide sequence of the sTRSV (FIG. 1A) starting at nt 20 and extending through nt 44 is used in the search, i.e. Loop 2 through Loop 4.

The identified sequence from the database is then aligned with the sTRSV ribozyme sequence. The sequences are then modeled to find structural parameters corresponding to Helices 3 and 4 followed by modeling to find the structural parameter corresponding to Loop 3. If these features are not found the sequence is discarded.

The identified sequence is then screened for the substrate binding portion of the catalyst, $3'F_4\text{-}L_1\text{-}F_3\text{-}5'.F_4$ and $F_3$ are separated by Loop 1 which has a sequence of at least four to seven nucleotides.

The substrate of the ribozyme is then identified. The entire sequence from which the ribozyme was identified is searched for a region corresponding to the target sequence, $5'\text{-}F_1\text{-}CS$ (Loop 5)-$F_2\text{-}3'$, wherein $F_3$ is substantially base paired with $F_2$ forming Helix 1 and $F_4$ is substantially base paired with $F_1$ thereby forming Helix 2 when the catalyst is bound to the substrate.

If the target sequence is not within the identified sequence then a substrate test panel (see Table 1 herein below) is synthesized such that $F_1$ and $F_2$ will base pair with $F_4$ and $F_3$ and Loop 5 is N*GUX where N can be any base pair and X is any base pair. From this test panel the substrate is identified.

The method allows for the identification of hairpin ribozymes with expanded repertoires of cleavage sites. As shown in Example 1, the method allows the recovery of ribozymes that have alternative sequences in Loop 5. Further, the method does not restrict the identification of sequences in the database to those that are homologous to the sTRSV ribozyme Loop 1. Nor is the identification restricted to those sequences that are homologous with Helices 1 and 2.

The above discussion provides a factual basis for the use of ribozymes that cleave an RNA substrate at a site which has a GUA sequence following the site of cleavage as well as methods for identifying/modeling new ribozymes with additional cleavage sites. The methods used with and the utility of the present invention can be shown by the following examples.

EXAMPLES

GENERAL METHODS:

Reactions and manipulations involving DNA techniques, unless stated otherwise, were performed as described in Sambrook et al., 1989, *Molecular Cloning: A Laboratory Manual*, Cold Spring Harbor Laboratory Press, incorporated herein by reference. Manipulations involving RNA techniques unless stated otherwise were performed as described in Uhlenbeck (1987) and Haseloff and Gerlack (1988, 1989).

Materials

Unless stated otherwise, the sources for materials used are as listed hereinbelow.

Enzymes and Chemicals. All restriction enzymes used were from either Bethesda Research Laboratories (BRL) or Boehringer Mannheim Biochemicals. The buffers for restriction enzymes were supplied by the manufacturer. T4DNA ligase and the sequencing kit were obtained from Pharmacia. The in vitro transcription kit and relevant enzymes were obtained from Promega. Bovine calf serum, antibiotics (penicillin and streptomycin), L-glutamine, sodium pyruvate, phosphate-buffered saline (PBS) and Dulbecco modified Eagle medium (DMEM) were purchased from GIBCO.

Enzymes and Chemicals: T4 DNA Ligase and all restriction enzymes used were from Bethesda Research Laboratories (BRL). T7 RNA Polymerase used was manufactured by US Biochemicals (USB). With the exception of T7 RNA Polymerase, the buffers for enzymes used were supplied by the manufacturer. Synthetic DNA templates used for in vitro transcriptions and cloning were produced using an Applied Biosystems 392 DNA synthesizer.

$P^{32}$ labelling

Substrate and ribozymes were labelled with a $P^{32}$-CTP by transcription from synthetic DNA templates using T7 RNA polymerase as previously described (Hampel and Tritz, 1989) and reaction products separated on 15–18% polyacrylamide gels in 7M urea.

Ribozyme Construction

Ribozymes were constructed by T7 transcription from complementary synthetic DNA templates. This was carried out as previously described (Hampel and Tritz, 1989).

Construction of vectors and plasmids containing ribozymes

Coding and non-coding strands for the ribozymes were synthesized and HPLC purified. The strands generally include an Eco RI site, the ribozyme coding region, a poly-T termination signal for RNA Polymerase III, and a Bam HI site. The two strands are then annealed by adding an equimolar amount of each and incubating in $H_2O$ at 90 C. for five minutes, then allowed to slowly cool down to room temperature over a 30-minute period. The resulting double-stranded fragment is then digested with Eco RI and Bam HI. The digestion products are run on an agarose gel, and the ribozyme coding fragment isolated and purified.

In one embodiment, plasmids are constructed generally using the method of Altschuler et al., 1992. A suitable plasmid source is digested with Eco RI and Bam HI, and the fragment isolated and purified as above. A ribozyme fragment is then ligated into the plasmid and the ligation mixture used to transform competent bacterial cells. Single colonies are selected and grown in CircleGrow bacterial media and plasmids extracted and purified by Sambrook's miniprep protocol (Sambrook et al., 1989). The plasmids were screened for incorporation of the ribozyme insert. A colony that incorporated the insert is then sequenced using the Sequenase Version 2.0 enzymes and protocol to verify proper DNA sequence.

Transfection of suitable host cells by the above vectors can then be undertaken by standard methods as described herein above and as set forth by Ojwang et al. (1992) and Yu et al. (1993).

Cleavage reaction.

Ribozyme and substrate, 125 nM each, were incubated for one hour at 37 C. in cleavage buffer containing 12 mM $MgCl_2$, 2 mM spermidine and 40 mM Tris, pH 7.5 at 37 C. (Hampel and Tritz, 1989). Reactions were terminated by addition of electrophoresis buffer containing 98% formamide and 10 mM EDTA. Separation of substrate and products was achieved by electrophoresis over a 15% polyacrylamide/7M urea gel in 1×TBE. The reaction result was analyzed by autoradiography. Reactants and products were excised from the gel and quantitated by scintillation counting in BioSafe II scintillation fluid (Research Products Intl. Co.).

Transcription Reactions

RNA was transcribed from oligodeoxynucleotide partial duplexes according to a modification of the method of Milligan et al. (1987) (Hampel et al. 1993). To improve transcription, GGG and GCG sequences were added to the 5' end of all ribozyme and substrate RNA sequences, respectively. Oligodeoxynucleotide sequences, complementary to the catalytic RNAs shown in FIG. 1 and to the substrate RNAs shown in Table 1, were synthesized with CCC or CGC and T7 promoter sequences at the 3' end on an Applied Biosystems Inc. 392 RNA/DNA synthesizer (Foster City, Calif.) according to standard techniques. Oligodeoxynucleotides were purified by HPLC and annealed to a T7 complement to form the transcription template. DNA template (500 ng) was combined with 4% PEG, 0.1% Triton X-100, 1 mM spermidine, 5 mM DTT, 40 mM Tris, 6 mM $MgCl_2$, 40 mM Tris (pH 8.0), each nucleoside triphosphate (1 mM) and 20–100 U of T7 RNA polymerase (Ambion or United States Biochemicals Corp.) in a 50 µl reaction volume. Alpha $^{32}$P-CTP (ICN) was used to label the transcripts. After 3 hours at 37 C., 2U of DNase (Ambion) was added to remove the DNA template. Transcribed RNA was purified on 10 or 15% polyacrylamide/7M urea electrophoresis gels for ribozymes or substrates, respectively, extracted from the gel matrix, and quantitated based on radioactive content.

Kinetic studies

Transcribed RNA was resuspended in water at initial concentrations ranging from 0.5 to 8 µM RNA. Kinetic reactions were performed in volumes ranging from 4 to 8 µl with substrate RNA concentrations ranging from 60 to 4000 nM, depending on the Km of the riboyzme-substrate complex. Ribozyme concentrations were kept as low as possible to allow multiple reaction turnovers and ranged from 1 to 7 nM. For each ribozyme/substrate complex, experimental conditions were established to approach and then exceed the Km by a factor of 2 to 4.

The more active ribozyme-substrate combinations required as little as 30 min for reaction, although ribozyme-substrate combinations with lower catalytic activity were incubated for up to six hours to allow product detection. To remain near the linear range, no more than 15% substrate cleavage was permitted in a given experiment. Cleavage was done in buffer containing 12 mM $MgCl_2$, 2 mM spermidine and 40 mM Tris, pH 7.5 at 37 C. (Hampel and Tritz, 1989). Reactions were terminated by addition of electrophoresis buffer containing 98% formamide and 10 mM EDTA. Separation of substrate and products was achieved by electrophoresis over a 15% polyacrylamide/7M urea gel in 1×TBE. The reaction result was analyzed by autoradiography. Reactants and products were excised from the gel and quantitated by scintillation counting in BioSafe II scintillation fluid (Research Products Intl. Co.).

Reaction velocities were calculated from product concentrations and incubation times. The kinetics of the ribozyme reactions were analyzed according to the Michaelis-Menten equation using a curve-fitting program (Tablecurve 2D v3 for win32, Jandel Scientific Software Co., San Rafael, Calif.) which derived Km and kcat values from reaction velocities and substrate concentrations. The $r^2$ determination of goodness of fit exceeded 0.90 in all cases. Data given are the mean of all trials.

Substrates sequences used.

All substrates had an additional GCG on the 5' terminus to optimize transcription. The number designation in the origin column corresponds to the nt# and designates mutations in that position with the nucleotide preceding the number being the nonmutated nucleotide and that following the number the changed nucleotide.

The native substrate sequences correspond to nucleotides 53–40 sTRSV, 52–39 sCYMV1, and 55–42 sArMV respectively from the original sequences. For this study, the numbering has been adopted such that nt #1 is the 5' terminus of these sequences.

TABLE 1

| Sequence† 1   8   14 | Origin | SEQ ID No: |
|---|---|---|
| UGACA*GUCCUGUUU | sTRSV | SEQ ID No:4 |
| UGACA*GUACUGUUU | sTRSV-C8A | SEQ ID No:5 |
| UGACA*GUGCUGUUU | sTRSV-C8G | SEQ ID No:6 |
| UGACA*GUUCUGUUU | sTRSV-C8U | SEQ ID No:7 |
| GCGCA*CUACUGUUU | sCYMV1 | SEQ ID No:8 |
| GCGCA*GUCCUGUUU | sCYMV1-A8C | SEQ ID No:9 |
| GCGCA*GUGCUGUUU | sCYMV1-A8G | SEQ ID No:10 |
| GCGCA*GUUCUGUUU | sCYMV1-A8U | SEQ ID No:11 |
| ACGCA*GUACUGUUU | sArMV | SEQ ID No:12 |
| CCGCA*GUACUGUUU | sArMV-A1C | SEQ ID No:13 |
| CCGCA*GUCCUGUUU | sArMV-A1C-A8C | SEQ ID No:14 |
| CCGCA*GUGCUGUUU | sArMV-A1C-A8G | SEQ ID No:15 |
| CCGCA*GUUCUGUUU | sArMV-A1C-A8U | SEQ ID No:16 |
| CCGCA*GUACUGUUG | sArMV-A1C-U14G | SEQ ID No:17 |
| GCGCA*GUACUGUUG | sCYMV1-U14G | SEQ ID No:18 |
| UGUGU*GUACUGCAAGC | sCYMV1 heterologous seq. | SEQ ID No:19 |

*The site of cleavage.
†Nucleotide number

EXAMPLE 1

Molecular modeling to identify new catalytic centers for sCYMV1 and sArMV ribozyme.

Sequence Homology

The data base on GenBank was searched for sequence homology to sTRSV hairpin ribozyme. Regions of sequence homology in the sequences of sArMV and sCYMV1 were identified and selected for further analysis. The identified sequences were each aligned with homologous sTRSV hairpin ribozyme sequences.

Structural Homology

Complete sequence homology was present in Helix 4 of the sTRSV hairpin ribozyme, allowing formation of an intact helix for the sCYMV1 model and sARMV model. In the Loop 2 region, six of seven nt were present allowing identification of Loop 2. In Loop 4 nine of ten nt were present allowing identification of Loop 4. When these three structures were formed a Loop 3 having 5 nt was defined for each ribozyme.

Continuation of the sequence both in the 5' and 3' directions determined a region of base pairing with 4 bp located exactly where Helix 3 is located in the sTRSV hairpin ribozyme. The sArMV sequence had a potential additional A:U base pair in this site, but applicants previously showed this base pair does not exist. Therefore, it was not placed in the sArMV model. The sCYMV1 sequence also has a potential G:C base pair at this site, but again for the above reasons, it was not included. Thus, Helix 3 is now defined.

The sequences of sArMV and sCYMV1 were continued in the 5' direction with the same number of nt as found in the sTRSV hairpin structure.

In the next step of the modeling protocol, a sequence elsewhere in the entire sequence of sArMV and sCYMVI respectively was searched for which was homologous to this sequence and which forms a 4 bp Helix 2 and a Helix 1 of indeterminate length with 4 unpaired nt between these two helices. This represents the potential substrate for the ribozyme-substrate model. Such a sequence was found for the sCYMV1 system, but only a 3 bp Helix 2 sequence could be found for the sArMV system.

When these sequences were paired with the potential ribozyme, it was found that both complexes had a 5 bp Helix 1 with a 4 nt unpaired sequence before Helix 2. Furthermore, three of the 4 nt in each of the loops (Loop 1 and Loop 5) were conserved. Helix 2 was 3 bp in the arabis system nd 4 bp in the chicory system.

The 3' end of the potential ribozyme was extended to leave two unpaired nt beyond Helix 3, by analogy with the sTRSV hairpin model. The results of this modeling are shown in FIGS. 1B–C.

EXAMPLE 2

The predicted functional domain has catalytic phosphodiesterase activity in a trans reaction, i.e., it cleaves a target RNA substrate. Thus, these are sCYMV1 and sArMV derived ribozymes.

Figure 2:
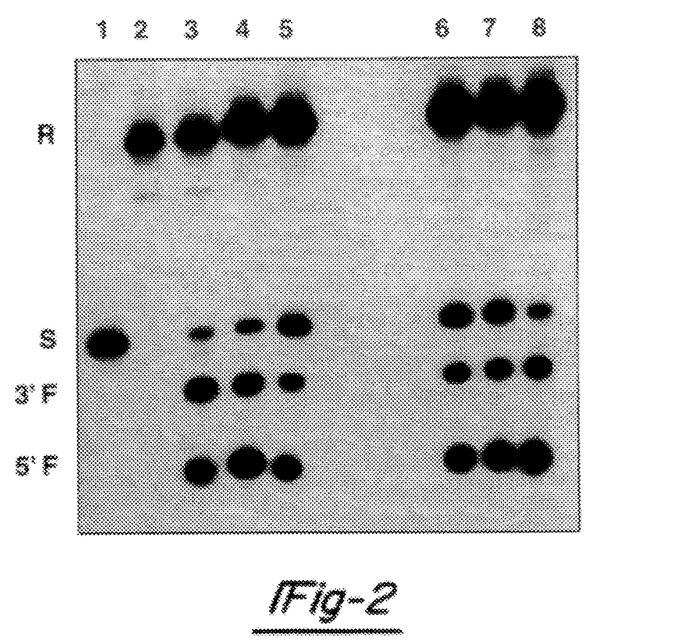
FIG. 2 is a scan of a slab gel electrophoresis showing substrate cleavage by ribozymes derived from sTRSV, sCYMV1 and sArMV sequences (sequences of the ribozymes are in FIG. 1 and the substrates are in FIG. 1 and Table 1), controls are STRSV substrate only (lane 1) and sTRSV ribozyme only (lane 2), cleavage of respective substrates by sTRSV (lane 3), sCYMV1 (lane 4), and sArMV (lanes 5 and 6) ribozymes and sCYMV1 ribozyme (lane 7) which both mismatch the substrate at the first nucleotide to give a 3 bp Helix 2, sArMV ribozyme cleavage of substrate sArMV-A1C (lane 8) in which substrate base A1 has been mutated to a C to give a 4bp Helix 2.

The ribozymes from sCYMV1 and sArMV have catalytic activity in a trans cleavage reaction as shown in FIG. 2. Under the reaction conditions used, the sCYMV1 ribozyme sequence cleaved its corresponding substrate (lane 4) to 88% completion, the sArMV ribozyme sequence cleaved its substrate to 60% completion (lanes 5 and 6), while the control sTRSV hairpin ribozyme cleaved to near completion, 85%, its corresponding substrate (lane 3). The experiments were repeated at least three times with similar results.

No substrate degradation was observed in controls under these experimental conditions in the absence of ribozyme (sTRSV, lane 1; data for sCYMV1 and sArMV substrate not shown). These results clearly show the sequences derived from sCYMV1 and sArMV are capable of phosphodiester cleavage of a corresponding target RNA substrate.

EXAMPLE 3

Helix 2 of the sArMV ribozyme can be engineered by extending it to 4 bp from the native 3 bp. The sArMV ribozyme has a G opposite an A in the first 5' base of the substrate in the proposed Helix 2 of the hairpin model. The nature of these two bases could be either a non-Watson-Crick A:G base pair or an A:G mismatch depending on the adjacent sequence (Santa Lucia et al., 1990). To further explore requirements in Helix 2 of the proposed structures, the A base in the substrate was mutated to a C in this position to give the substrate sArMV-A1C. If the models are correct, this would allow formation of a C:G base pair and thus a 4 bp Helix 2. The sArMV-A1C substrate sequence served as a substrate for the sArMV ribozyme (FIG. 2, lane 8) with cleavage to 90% completion. This data clearly show that for the sArMV system, a proposed conventional 4 bp Helix 2 is catalytically active.

To further investigate the nature of mismatches in this position, applicants tested a mismatch in the chicory system. When the original sArMV substrate was tested with the sCYMV1 ribozyme, cleavage also occurred with this ribozyme (FIG. 2, lane 7) to 70% completion under these conditions. This combination would give a proposed A:C mismatch in this first position of Helix 2 for the chicory system resulting in a 3 bp Helix 2.

EXAMPLE 4

Kinetic analyses of these ribozyme-substrate combinations follow true Michaelis-Menten kinetics and show excellent catalytic efficiencies.

The catalytic parameters Km and kcat were determined for the sCYMV1 and sArMV ribozymes and various substrates under conditions of substrate excess with multiple turnover events for the ribozyme as shown in Table 2.

TABLE 2

Kinetic parameters of ribozyme cleavage

| Ribozyme | Substrate | kcat (min$^{-1}$) | Km (nM) | kcat/Km ($\times 10^4$ M$^{-1}$min$^{-1}$) |
|---|---|---|---|---|
| sTRSV | sTRSV | 0.36 | 96 | 360 |
| sCYMV1 | sCYMV1 | 0.32 | 400 | 80 |
| sArMV | sArMV | 0.29 | 2,600 | 11 |
| sCYMV1 | sArMV | 0.19 | 1,400 | 14 |
| sArMV | sArMV-A1C | 0.26 | 880 | 30 |
| sArMV | sArMV-A1C-U14G | 0.27 | 580 | 47 |
| sCYMV1 | sCYMV1-U14G | 1.2 | 3000 | 40 |

Thus, these kinetic values represent true Michaelis-Menten catalytic parameters. Extensive ribozyme turnover was observed for both the sCYMV1 and sArMV sequences, and the determined kcat values were similar to the kcat determined for a sTRSV in side-by-side experiments. However, Km values for the sCYMV1 and sArMV ribozymes, 400 nM and 2600 nM, respectively, were higher than the value of 96 nM for sTRSV by a factor of four for the sCYMV1 ribozyme and a factor of more than 20 for the sArMV ribozyme.

A likely contributing factor to the extremely high Km for the sArMV ribozyme was due to the possible A:G mismatch in Helix 2 at position one of the substrate to give a 3 bp Helix 2. To test this in more detail, the first base in the sArMV substrate was mutated from A1C to allow a C:G base pair in this position and thus give a proposed 4 bp Helix 2. This substrate sequence, sArMV-A1C, lowered Km by a factor of 3 and had no effect on kcat (Table 2, line 5). This gave an overall 3× increase in catalytic efficiency.

In a converse analysis, the Km for the sCYMV1 ribozyme was increased by a factor of over three when the A:C mismatch was introduced into its substrate (this is the sArMV substrate of Table 1) to give a 3 bp Helix 2. This change from a 4 bp to a 3 bp Helix 2 gave overall reduction in catalytic efficiency of 6× (Table 2, line 4). Taken together, these results suggest that optimal activity is obtained with a 4 bp Helix 2 and, additionally, the proposed Helix 2 structure in the SCYMV1 and sARMV ribozyme-substrate model is likely correct.

EXAMPLE 5

The sCYMV1 and sArMV derived hairpin ribozymes have a GUA sequence preference following the cleavage site in the substrate.

Applicants previously showed STRSV hairpin ribozyme has a GUC preference. Thus, a new class of targetable substrates has been discovered. The GUX sequence is the sequence immediately following the cleavage site of the substrate. The sTRSV system has GUC in this position while the sArMV and sCYMV1 systems have a change in the base at position #8 to give GUA in the native sequence.

A panel of substrates (Table 1) was constructed for each of the sTRSV, sCYMV1 and sArMV ribozymes to examine the effects of varying nucleotide 8 in the substrate. These are GUX variants. To make the comparison useful, the sArMV substrate used had a 4 bp Helix 2 to make it equivalent to the sTRSV and sCYMV1 systems.

Figure 3:
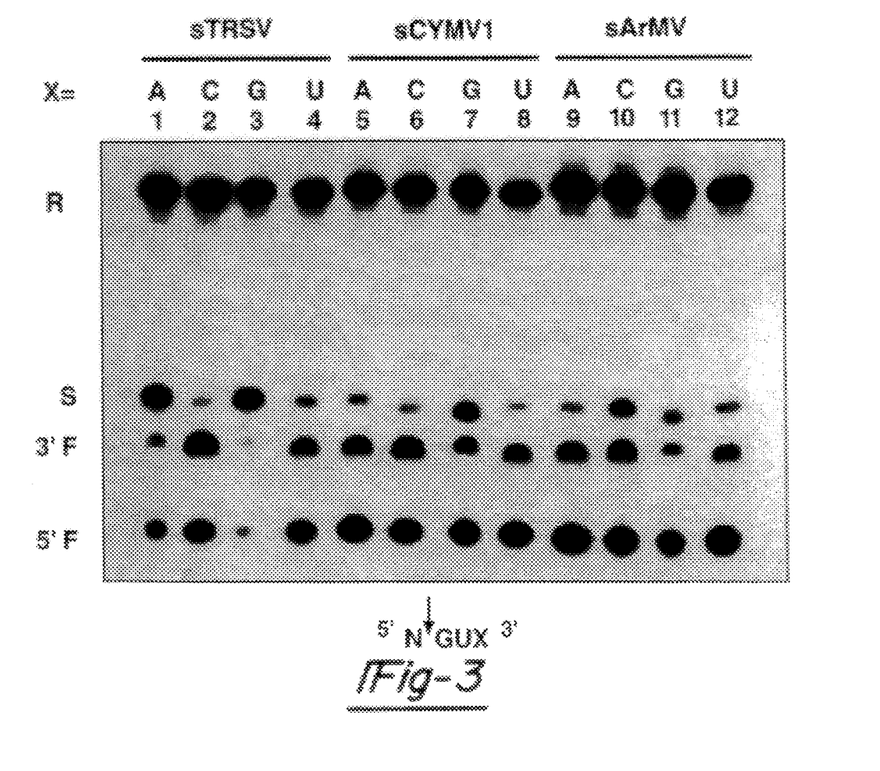
FIG. 3 is a scan of a slab gel electrophoresis showing a comparison of sTRSV, sCYMV1 and sArMV ribozyme cleavage of substrates modified in GUX at the target site (the X base is at position 8 in the substrate), sTRSV ribozyme cleavage of sTRSV-C8A (lane 1), native STRSV (lane 2), sTRSV-C8G (lane 3) and sTRSV-C8U (lane 4), sCYMV1 ribozyme cleavage of sCYMV1 native substrate (lane 5), sCYMV1-A8C (lane 6), sCYMV1-A8G (lane 7) and sCYMV1-A8U (lane 8), sArMV ribozyme cleavage of sArMV substrate sArMV-A1C (lane 9), sArMV-A1C-A8C (lane 10), sArMV-A1C-A8G (lane 11) and sArMV-A1C-A8U (lane 12)

At an equimolar ratio of ribozyme to substrate (125 nM each) and for one hour, cleavage occurred with all variants in position (FIG. 3). Under the experimental conditions of FIG. 2, which include a 1:1 ribozyme:substrate ratio, sTRSV ribozyme cleaved sTRSV substrate C8A to 28% completion; C8 to 93% completion; C8G to 18% completion; and C8U to 87% completion. The sCYMV1 ribozyme cleaved sCYMV1 substrate A8 to 92% completion; A8C to 92% completion; C8G to 73% completion and C8U to 92% completion. sArMV ribozyme cleaved sArMV-A1C-A8 to 93% completion; A1C-A8C to 80% completion; A1C-A8G to 80% completion and A1C-A8U to 90% completion. The sArMV ribozyme also cleaved A8-mutated substrates mismatched at nucleotide 1 with the same relative nucleotide preferences, but to a lesser extent (data not shown). These experiments were repeated four times with similar results. This data clearly shows GUX sequences can be cleaved by the sArMV and sCYMV1 ribozymes.

True Michaelis-Menten kinetic parameters, Km, kcat, and kcat/Km (catalytic efficiency), for ribozyme cleavage of these GUX substrate mutants were determined (Table 3).

TABLE 3

Comparison of the efficiency of GUX cleavage by sTRSV, sCYMV1 and sArMV ribozymes.

| Ribozyme | Substrate | GUX | kcat (min$^{-1}$) | Km (nm) | kcat/Km ($\times 10^4$ M$^{-1}$min$^{-1}$) |
|---|---|---|---|---|---|
| sTRSV | sTRSV-C8A | GUA | 0.038 | 2,500 | 2 |
|  | sTRSV | GUC | 0.36 | 96 | 360 |
|  | sTRSV-C8G | GUG | 0.01 | 540 | 2 |
|  | sTRSV-C8U | GUU | 0.045 | 390 | 12 |
| sCYMV1 | sCYMV1 | GUA | 0.32 | 400 | 80 |
|  | sCYMV1-A8C | GUC | 0.14 | 1,500 | 9 |
|  | sCYMV1-A8G | GUG | >0.5 | >6,500 | — |
|  | sCYMV1-A8U | GUU | >0.5 | >10,000 | — |
| sArMV | sArMV-A1C | GUA | 0.26 | 880 | 30 |
|  | sArMV-A1C-A8C | GUC | 0.22 | 5,400 | 4 |
|  | sArMV-A1C-A8G | GUG | 0.26 | 1,700 | 15 |
|  | sArMV-A1C-A8U | GUU | 0.40 | 3,000 | 10 |

For the sTRSV hairpin ribozyme, the native GUC sequence is clearly preferred with GUC having a catalytic efficiency at least 30× greater than that of the GUU, GUA and GUG sequences.

For the sCYMV1 sequence, the native GUA in the substrate is clearly preferred, with a catalytic efficiency 9× greater than the corresponding GUC sequence. The sCYMV1 substrates with GUG and GUU had such high Km values that it was not possible to determine them. Thus, these substrates were cleaved at a low efficiency.

For the sArMV system, with a 4 bp Helix 2, the native GUA is also the preferred sequence in the substrate. However, the GUG sequence has a catalytic efficiency of nearly ½ that of the native GUA. The GUU has a catalytic efficiency of about ⅓ that of the preferred GUA in the substrate and the GUC sequence is very poor for the sArMV system.

These data show that mutations in position 8 of the sTRSV substrate from C to G, U or A produce reduction in catalytic efficiency which confirms earlier reports that the GUC sequence is preferred (Hampel et al., 1990; Anderson et al., 1994). The preference order at substrate position 8 based on the catalytic efficiencies are C>U>G=A for sTRSV. For the sCYMV1 system, the GUA is the preferred sequence with order of preference in position 8 being A>C,G,U. For sArMV with a 4 bp Helix 2, the order of preference in this position is A>G>U>C. The decrease in catalytic efficiency for the sCYMV1 and sArMV substrates is primarily associated with an increase in Km.

The GUA containing substrate sequences for the chicory system had a catalytic efficiency 20× greater than that of the corresponding GUA sequence for the sTRSV system. The arabis system with GUA and a 4 bp Helix 2, had a catalytic efficiency 15× greater than that of the GUA in the sTRSV system. This clearly shows that all three systems prefer their native sequences at this position, and that, furthermore, greatly improved cleavage of GUA containing substrates is seen in both the chicory and arabis systems over the sTRSV system. This identifies a new class of substrates containing GUA at the cleavage site, for targeting in gene therapy applications.

EXAMPLE 6

The sArMV ribozyme cleaves GUG sequences with reasonable efficiency. The sArMV ribozyme also cleaves GUG containing sequences at significant catalytic efficiencies.

These catalytic efficiencies are as much as 50% of the native GUA containing sequence and 7× greater than cleavage of GUG containing sequences by the sTRSV hairpin system (Table 3). The hammerhead ribozyme does not cleave GUG sequences well (Perriman et al., 1992).

EXAMPLE 7

Helix 1 of both the sArMV and sCYMV1 ribozymes can be extended from the native 5 bp to 6 bp.

Substrate-ribozyme combinations were made which extended the native 5 bp Helix 1 of both the sArMV and sCYMV1 ribozymes to 6 bp. This was done with a U14G mutation in both substrates allowing a G:C base pair at the end of Helix 1. The corresponding substrate for the sARMV ribozyme is then named sArMV-A1C-U14G (Table 1). This will then have a 4 bp Helix 2 and a 6 bp Helix 1. The corresponding substrate for the sCYMV1 ribozyme is sCYMV1-U14G, which again, gives a G:C base pair at the start of Helix 1 to give a 6 bp Helix 1.

Kinetic analyses show 1.5× increase in catalytic efficiency (kcat/Km) for this substrate over the 5 bp Helix 1 combination with the sArMV ribozyme (Table 2). This increase was due to a decrease in Km with no effect on kcat. Thus, Helix 1 can be extended for the sArMV system resulting in an increase in catalytic efficiency. The sCYMV1 ribozyme-substrate combination is also catalytically active when Helix 1 is extended from 5 bp to 6 bp (Table 2). The resulting catalytic efficiency for the 6 bp Helix 1 ($40 \times 10^4 M^{-1} min^{-1}$), however, was less than for the 5 bp Helix 1 ($80 \times 10^4 M^{-1} min^{-1}$).

These data show that Helix 1 can be extended to variable length, and non-native substrates can be cleaved by these two new ribozymes.

EXAMPLE 8

The sCYMV1 ribozyme can be engineered to cleave a completely non-native heterologous substrate sequence.

Figure 4:
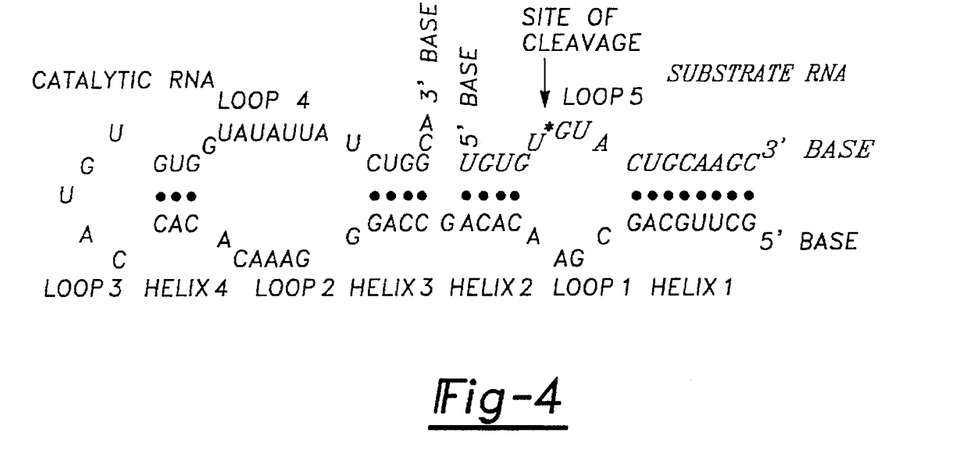
FIG. 4 is a schematic representation of an engineered ribozyme, shown complexed to a substrate based on the sCYMV1 derived hairpin ribozyme, Helix 1 was made 8 bp and a U rather than an A is found before the GUC at the substrate cleavage site.

To determine whether the sCYMV1 system could be engineered to cleave a completely non-native sequence, a sCYMV1 ribozyme was engineered to base pair to the sequence flanking the U*GUA of a new target sequence (sCYMV1 heterologous sequence in Table 1). The ribozyme substrate combinations are shown in FIG. 4.

Figure 5:
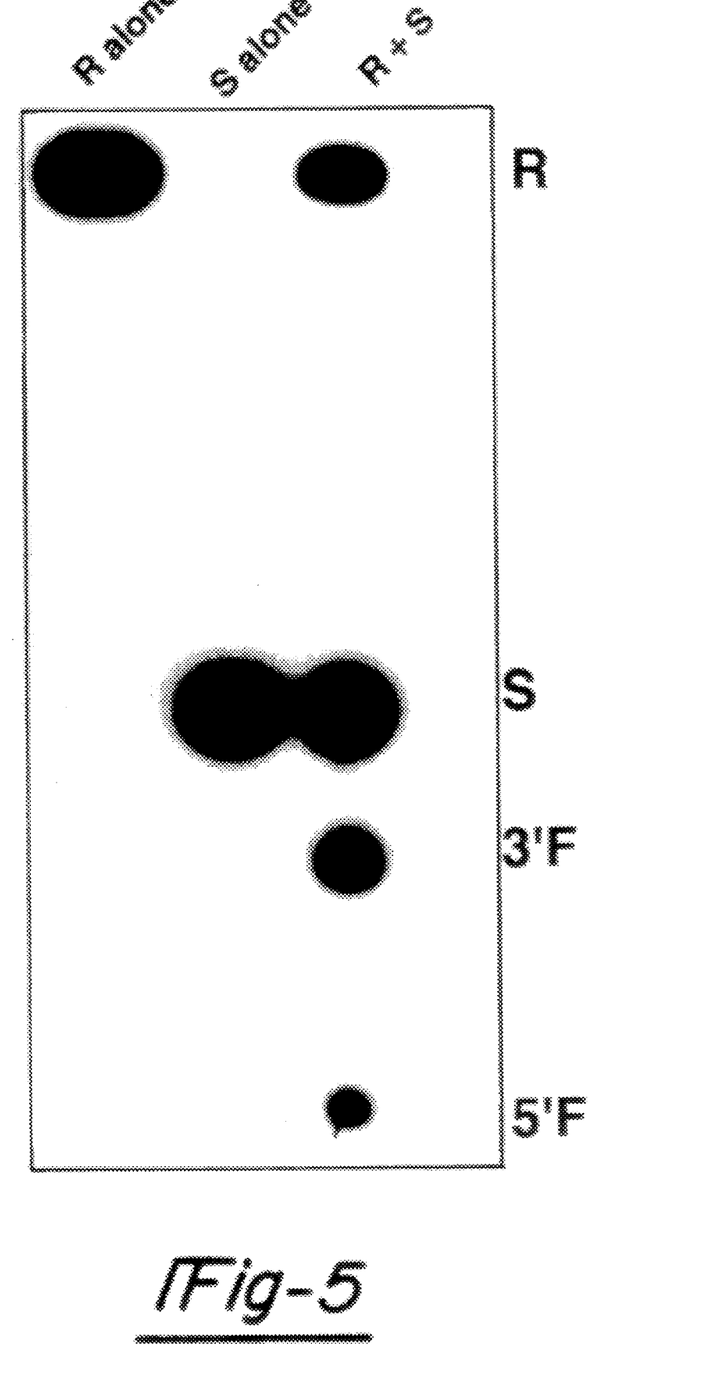
FIG. 5 is a scan of a slab gel electrophoresis of cleavage of substrate by engineered sCYMV1 hairpin ribozyme (lane 3) and controls ribozyme only (lane 1) and substrate (lane 2) incubated alone under the same conditions, (R) ribozyme, (S) substrate, (3'F) 3' cleavage fragment, (5'F) 5' cleavage fragment.

A cleavage assay was carried out as described Example 4. The engineered sCYMV1 ribozyme cleaved the heterologous sequence in a catalytic reaction (FIG. 5). Cleavage of substrate went to 23% completion in two hours at 37° C. using 15 nM ribozyme and 100 nM substrate. This is 1.6 turnovers during the course of the reaction and shows true catalysis.

This experiment shows cleavage of a GUA containing heterologous sequence with a variable Helix 1 length. Thus, the sCYMV1 ribozyme can be engineered to cleave heterologous substrates.

Throughout this application various publications are referenced. Full citations for the referenced publications not cited herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Altschuler et al. (1992) "Method for generating transcripts with defined 5' and 3' termini by autolytic processing", *Gene*, 122:85–90

Anderson et al. (1994) "Mutagenesis of the hairpin ribozyme," *Nucleic Acids Res*, 22:1096–1100

Berzal-Harranz et al. (1993) "Essential nucleotide sequences and secondary structure elements of the hairpin ribozyme", *EMBO J.* 12:2567–2573

Buzayan et al. (1986) "Nucleotide Sequence of Satellite Tobacco Ringspot Virus RNA and Its Relationship to Multimeric Forms", *Virology* 151:186–199

Cech (1986) "RNA as an Enzyme", *Scientific American*, 255:64–75

Cech (1990) "Self-Splicing of Group I Introns", *Annu. Rev. Biochem.* 59:543–568

Fritsch et al. (1993) "Properties of satellite RNA of nepoviruses," *Biochemie* 75:561–567

Gilboa et. al., "Transfer and expression of cloned genes using retroviral vectors. *BioTechniques* 4(6):504–512, 1986.

Hampel and Tritz (1989) "RNA Catalytic Properties of the Minimum (−) sTRSV Sequence", *Biochemistry* 28:4929–4933

Hampel et al. (1990) "Hairpin catalytic RNA model: evidence for helices and sequence requirement for substrate RNA", *Nucleic Acids Research* 18:299–304

Hampel et al. (1993) "The Hairpin Ribozyme", *Methods: A Companion to Methods in Enzymology* 5:37–42

Haseloff and Gerlach (1988) "Simple RNA enzymes with new and highly specific endoribonuclease activities", *Nature* 334:585–591

Haseloff and Gerlach (1989) "Sequences required for self-catalyzed cleavage of the satellite RNA of tobacco ringspot virus", *Gene* 82:43–52

Kaper et al. (1988) "Nucleotide sequence predicts circularity and self-cleavage of 300-ribonucleotide satellite of arabis mosaic virus", *Biochem. Biophys. Res. Com* 154:318–325

Milligan et al. (1987) "Oligoribonucleotide synthesis using T7 RNA polymerase and synthetic DNA templates", *Nucleic Acids Res.*, 15:8783–8798

Ojwang et al. (1992) "Inhibition of human immunodeficiency virus type-I (HIV-1) expression by a hairpin ribozyme", *Proc. Nat. Acad. Sci. USA* 89:10802–10806

Perriman et al. (1992) "Extended target-site specificity for a hammerhead ribozyme", *Gene* 113:157–163

Rubino et al. (1990) "Nucleotide sequence and structural analysis of two satellite RNAs associated with chicory yellow mottle virus," *J. General Virology* 7:1897–1903

Sambrook et al. (1989) Molecular Cloning: *A Laboratory Manual*, Cold Spring Harbor Laboratory Press, New York, 1:1.25–1.28

Santa Lucia et al. (1990) "Effects of GA mismatches on the structure and thermodynamics of RNA internal loops", *Biochemistry* 29:8813–8819

Sullivan (1994) "Development of Ribozymes for Gene Therapy", *J. Investigative Dermatology (Suppl)* 103:95S Symons (1989) "Self-cleavage of RNA in the replication of small pathogens of plants and animals", *TIBS* 14:445–450

Symons (1992) "Small Catalytic RNAs", *Annu. Rev. Biochem.* 61:641–671

Uhlenbeck (1987) "Small catalytic oligoribonucleotide", *Nature* 328:596–600

Yamada et al. (1994) "Intracellular immunization of human T cells with hairpin ribozyme against human immunodeficiency virus type 1", *Gene Therapy* 1:38–45

Yu et al. (1993) "A hairpin ribozyme inhibits expression of diverse strains of human immunodeficiency virus type 1" *Proc. Nat. Acad. Sci. USA* 90:6340–6344

Wong-Staal and Nabel (1994) "Is HIV's Achilles Heel Hidden in its Genes", *HIV Advances in Res. and Therapy* 4:3–8

---

What is claimed is:

1. A ribozyme modeled from negative strands of satellite RNA from chicory yellow mottle virus (sCYMVI) including a hairpin portion and binding sites for cleaving an RNA substrate at a site which has a GUA sequence following the site of cleavage.

2. The ribozyme as set forth in claim 1 having a two-dimensional configuration as set forth in FIG. 1B and a nucleotide sequence as set forth in SEQ ID No:2.

3. A ribozyme modeled from negative strands of satellite RNA from arabis mosaic virus (sArMV) including a hairpin portion and binding sites for cleaving an RNA substrate at a site selected from the group consisting of a GUA sequence following the site of cleavage, a GUG sequence following the site of cleavage, and a GUU sequence following the site of cleavage.

4. The ribozyme as set forth in claim 3 having a two dimensional configuration as set forth in FIG. 1C and a nucleotide sequence as set forth in SEQ ID No:3.

5. A vector comprising a DNA sequence encoding said catalytic RNA according to claims 1 and 3, said DNA being operatively linked to expression control sequences.

6. A host cell transformed with a vector according to claim 5 wherein said cell is capable of expressing said catalytic RNA.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc ="RIBOZYME"

( v i ) ORIGINAL SOURCE:
        ( A ) ORGANISM: Tobacco ringspot virus     ( x i ) SEQUENCE DESCRIPTION: SEQ ID NO:1:

AAACAGAGAA GUCAACCAGA GAAACACACG UUGUGGUAUA UUACCUGGUA    50

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc ="RIBOZYME"

( v i ) ORIGINAL SOURCE:
        ( A ) ORGANISM: chicory yellow mottle virus     ( x i ) SEQUENCE DESCRIPTION: SEQ ID NO:2:

```
CAACAGCGAA  GCGCGCCAGG  GAAACACACC  AUGUGUGGUA  UAUUAUCUGG  CA                    52
```

(2) INFORMATION FOR SEQ ID NO:3:

(i) SEQUENCE CHARACTERISTICS:
        (A) LENGTH: 52 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="RIBOZYME"

(vi) ORIGINAL SOURCE:
        (A) ORGANISM: Arabis mosaic virus     (xi) SEQUENCE DESCRIPTION: SEQ ID NO:3:

```
CAACAGCGAA  GCGGAACGGC  GAAACACACC  UUGUGUGGUA  UAUUACCCGU  UG                    52
```

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Ribozyme substrate"

(xi) SEQUENCE DESCRIPTION: SEQ ID NO:4:

```
UGACAGUCCU  GUUU                                                                  14
```

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Ribozyme substrate"

(xi) SEQUENCE DESCRIPTION: SEQ ID NO:5:

```
UGACAGUACU  GUUU                                                                  14
```

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc ="Ribozyme substrate"

(xi) SEQUENCE DESCRIPTION: SEQ ID NO:6:

```
UGACAGUGCU  GUUU                                                                  14
```

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid ( A ) DESCRIPTION: /desc ="Ribozyme substrate"

( x i ) SEQUENCE DESCRIPTION: SEQ ID NO:7:

UGACAGUUCU GUUU											14

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Ribozyme substrate"

( x i ) SEQUENCE DESCRIPTION: SEQ ID NO:8:

GCGCACUACU GUUU											14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Ribozyme substrate
            sequence"

( x i ) SEQUENCE DESCRIPTION: SEQ ID NO:9:

GCGCAGUCCU GUUU											14

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Ribozyme substrate"

( x i ) SEQUENCE DESCRIPTION: SEQ ID NO:10:

GCGCAGUGCU GUUU											14

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Ribozyme substrate"

( x i ) SEQUENCE DESCRIPTION: SEQ ID NO:11:

GCGCAGUUCU GUUU											14

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear (i i) MOLECULE TYPE: other nucleic acid
        (A) DESCRIPTION: /desc ="Ribozyme substrate"

(x i) SEQUENCE DESCRIPTION: SEQ ID NO:12:

ACGCAGUACU GUUU                                                                           14

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="Ribozyme substrate"

(x i) SEQUENCE DESCRIPTION: SEQ ID NO:13:

CCGCAGUACU GUUU                                                                           14

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="Ribozyme substrate"

(x i) SEQUENCE DESCRIPTION: SEQ ID NO:14:

CCGCAGUCCU GUUU                                                                           14

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="Ribozyme substrate"

(x i) SEQUENCE DESCRIPTION: SEQ ID NO:15:

CCGCAGUGCU GUUU                                                                           14

(2) INFORMATION FOR SEQ ID NO:16:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="Ribozyme substrate"

(x i) SEQUENCE DESCRIPTION: SEQ ID NO:16:

CCGCAGUUCU GUUU                                                                           14

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear -continued ( i i ) MOLECULE TYPE: other nucleic acid
( A ) DESCRIPTION: /desc ="Ribozyme substrate"

( x i ) SEQUENCE DESCRIPTION: SEQ ID NO:17:

CCGCAGUACU GUUG 14

( 2 ) INFORMATION FOR SEQ ID NO:18:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Ribozyme substrate"

( x i ) SEQUENCE DESCRIPTION: SEQ ID NO:18:

GCGCAGUACU GUUG 14

( 2 ) INFORMATION FOR SEQ ID NO:19:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Ribozyme substrate"

( v i ) ORIGINAL SOURCE:
( A ) ORGANISM: Human papillomavirus type 16

( x i ) SEQUENCE DESCRIPTION: SEQ ID NO:19:

UGUGUGUACU GCAAGC 16